United States Patent
von Laer

(10) Patent No.: US 7,790,870 B1
(45) Date of Patent: Sep. 7, 2010

(54) MEMBRANE-ANCHORED GP41 PEPTIDES THAT INHIBIT SUBSEQUENT HIV VIRAL ENTRY

(75) Inventor: Meike-Dorothee von Laer, Hamburg (DE)

(73) Assignee: Heinrich-Pette-Institut, Hamburg (DE)

( * ) Notice: Subject to any disclaimer, the term of this patent is extended or adjusted under 35 U.S.C. 154(b) by 1605 days.

(21) Appl. No.: 10/148,064

(22) PCT Filed: Nov. 24, 2000

(86) PCT No.: PCT/EP00/11733

§ 371 (c)(1),
(2), (4) Date: Oct. 1, 2002

(87) PCT Pub. No.: WO01/37881

PCT Pub. Date: May 31, 2001

(30) Foreign Application Priority Data

Nov. 25, 1999 (DE) ................................ 199 57 838

(51) Int. Cl.
*C07H 21/04* (2006.01)
*A01N 43/04* (2006.01)
*A61K 31/70* (2006.01)
*C12N 15/00* (2006.01)
*C07K 14/00* (2006.01)
*C07K 17/00* (2006.01)

(52) U.S. Cl. .................... 536/23.4; 536/23.5; 514/44 R; 435/320.1; 530/350

(58) Field of Classification Search ................... 514/44; 424/93.1; 536/23.1, 24.2, 23.4
See application file for complete search history.

(56) References Cited

U.S. PATENT DOCUMENTS 5,851,828 A 12/1998 Seed et al. .................. 435/328
6,545,124 B1 * 4/2003 Bell et al. ................... 530/326

FOREIGN PATENT DOCUMENTS

WO WO 96/30523 10/1996

OTHER PUBLICATIONS

Wild, et al. (1994) Proc. Natl. Acad. Sci., USA, 91: 9770-74.*
Hildinger, et al. (2001) J. Virol., 75(6): 3038-42.*
Rudinger (1976) Peptide Hormones, University Park Press, Baltimore, MD., pp. 1-7.*
Bowie, et al. (1990) Science, 247 : 1306-10.*
Deonarain (1998) Expert Opin. Ther. Pat., 8: 53-69.*
Verma (1997) Nature, 389: 239-242.*
Eck et al. (1996) Goodman & Gilman's The Pharmacological Basis of Therapeutics, McGraw-Hill, New York, NY., pp. 77-101.*
Gorecki (2001) Expert Opin. Emerging Drugs 6(2): 187-98.*
Fehse, et al. (1997) Human Gene Therapy, 8: 1815-24.*
Jiang, et al: (1999) Journal of Virological Methods, 80: 85-96.*
Hareuveni, et al. (1990) Proceedings of the National Academy of Science, 87: 9498-502.*
Stewart, et al. (1999) Proceedings of the National Academy of Science, 96(21): 12039-43.*
Ernst, et al. (1998) Nucleic Acids Research, 26(7): 1718-23.*
Hrycyna, et al. (1998) Biochemistry, 37: 13660-73.*
Donnelly, et al. (1999) Experimental Hematology, 27: 788-96.*
Fleury, et al. (1999) Nature Structural Biology, 6(6): 530-34.*
Hildinger, et al. (1998) Human Gene Therapy, 9: 33-42.*
Song, et al. (1998) Proc. Natl. Acad. Sci., USA, 95: 14384-88.*
Frey, et al. (1998) Schweiz Med. Wochenschr., 128(42): 1587-92 (Abstract Only).*
Kent, et al. (1998) Journal of Virology, 72(12): 10180-88.*
Kleiman, et al. (1998) Gene Therapy, 5(5): 671-76.*
Kondo, et al. (1998) Gene Therapy, 5(5): 575-82.*
Andrew, et al. (1992) Vaccine, 10(3): 185-91 (Abstract Only).*
Chan et al., "Evidence that a prominent cavity in the coiled coil of HIV type 1 gp41 is an attractive drug target," *Proc. Natl. Acad. Sci. USA* 95:15613-15617 (1998).
Hildinger et al., "FMEV vectors: both retroviral long terminal repeat and leader are important for high expression in transduced hematopoietic cells," *Gene Therapy* 5:1575-1579 (1998).
Joshi et al., "A Core Trimer of the Paramyxovirus Fusion Protein: Parallels to Influenza Virus Hemagglutinin and HIV-1 gp41," *Virology* 248:20-34 (1988).
Muñoz-Barroso et al., "Role of the Membrane-Proximal Domain in the Initial Stages of Human Immunodeficiency Virus Type 1 Envelope Glycoprotein-Mediated Membrane Fusion," *Journal of Virology* 73:6089-6092 (1999).
Salzwedel et al., "A Conserved Tryptophan-Rich Motif in the Membrane-Proximal Region of the Human Immunodeficiency Virus Type 1 gp41 Ectodomain Is Important for Env-Mediated Fusion and Virus Infectivity," *Journal of Virology* 73:2469-2480 (1999).
Egelhofer et al., "Inhibition of Human Immunodeficiency Virus Type 1 Entry in Cells Expressing gp41-Derived Peptides", *Journal of Virology*, 78:568-575 (2004).

* cited by examiner

*Primary Examiner*—Robert M Kelly
(74) *Attorney, Agent, or Firm*—Arnold & Porter LLP

(57) ABSTRACT

The invention relates to the genetically engineered treatment of an HIV infection by the expression of membrane-anchored gp41 peptides. With this treatment vectors are made available for the first time which code for a fusion protein that contains a peptide derived from gp41 of HIV and a carboxy terminal by means of a trans-membrane anchor tagged to a flexible linker.

20 Claims, 5 Drawing Sheets

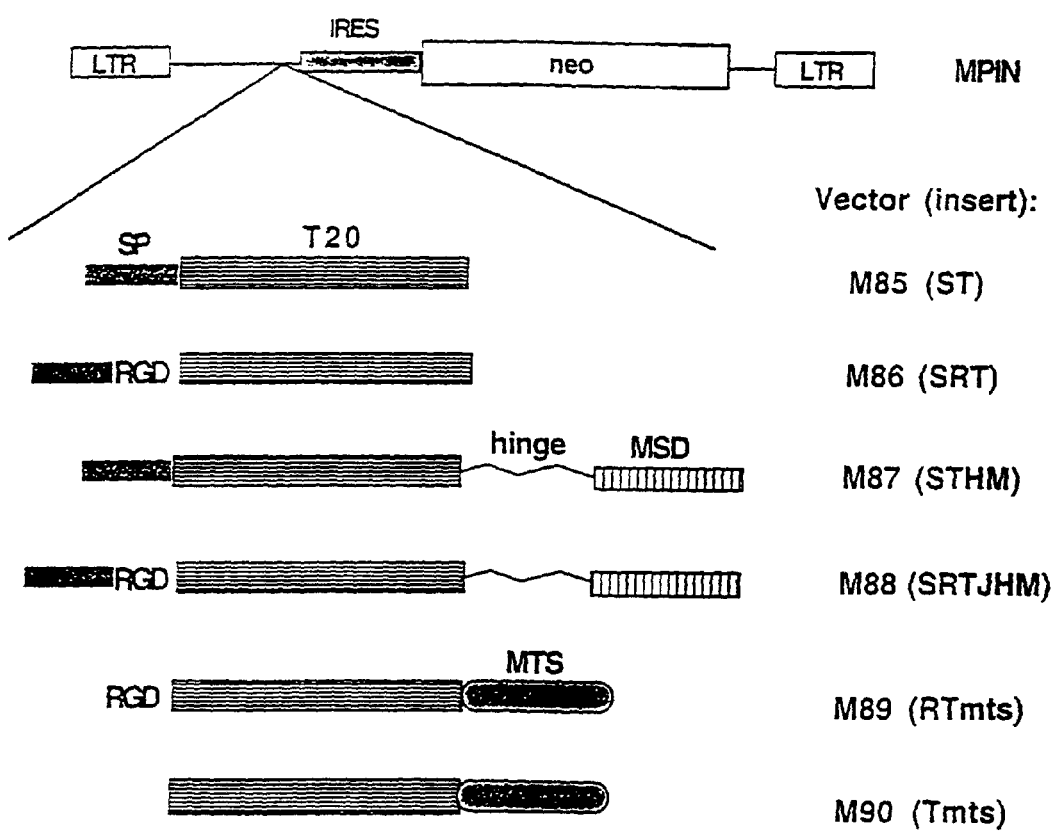

Figure 4:
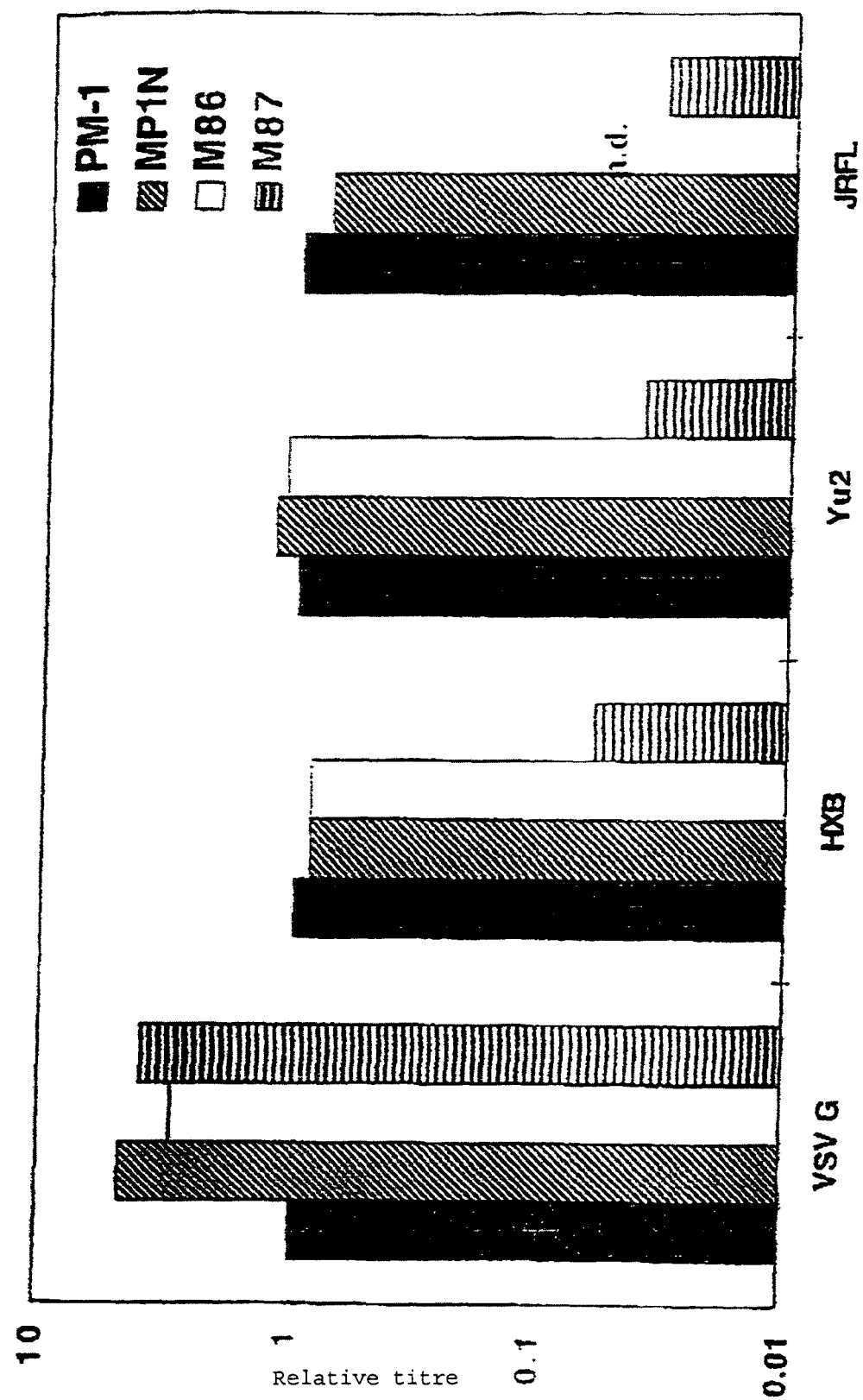

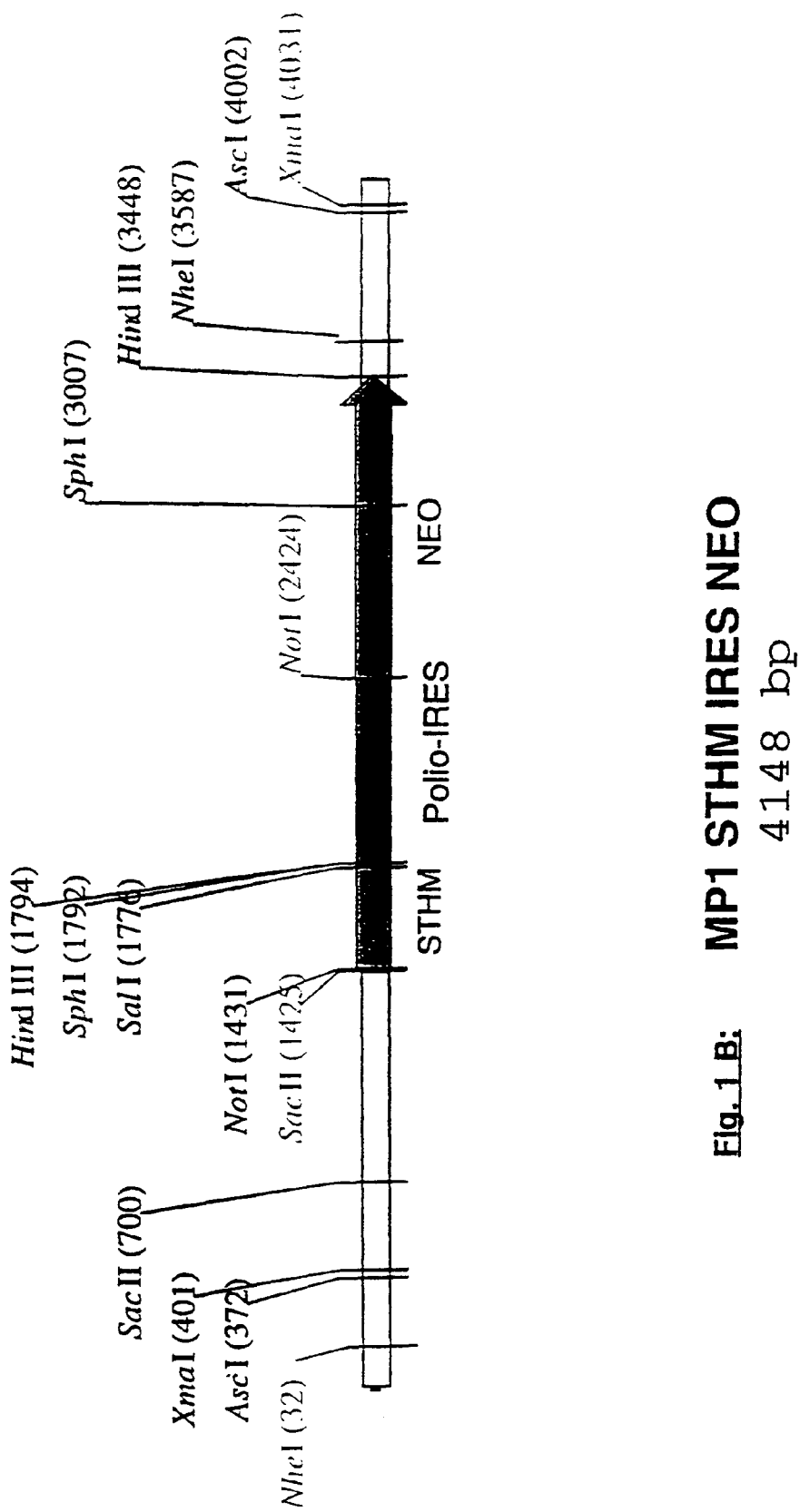
Fig. 1 B: MP1 STHM IRES NEO
4148 bp

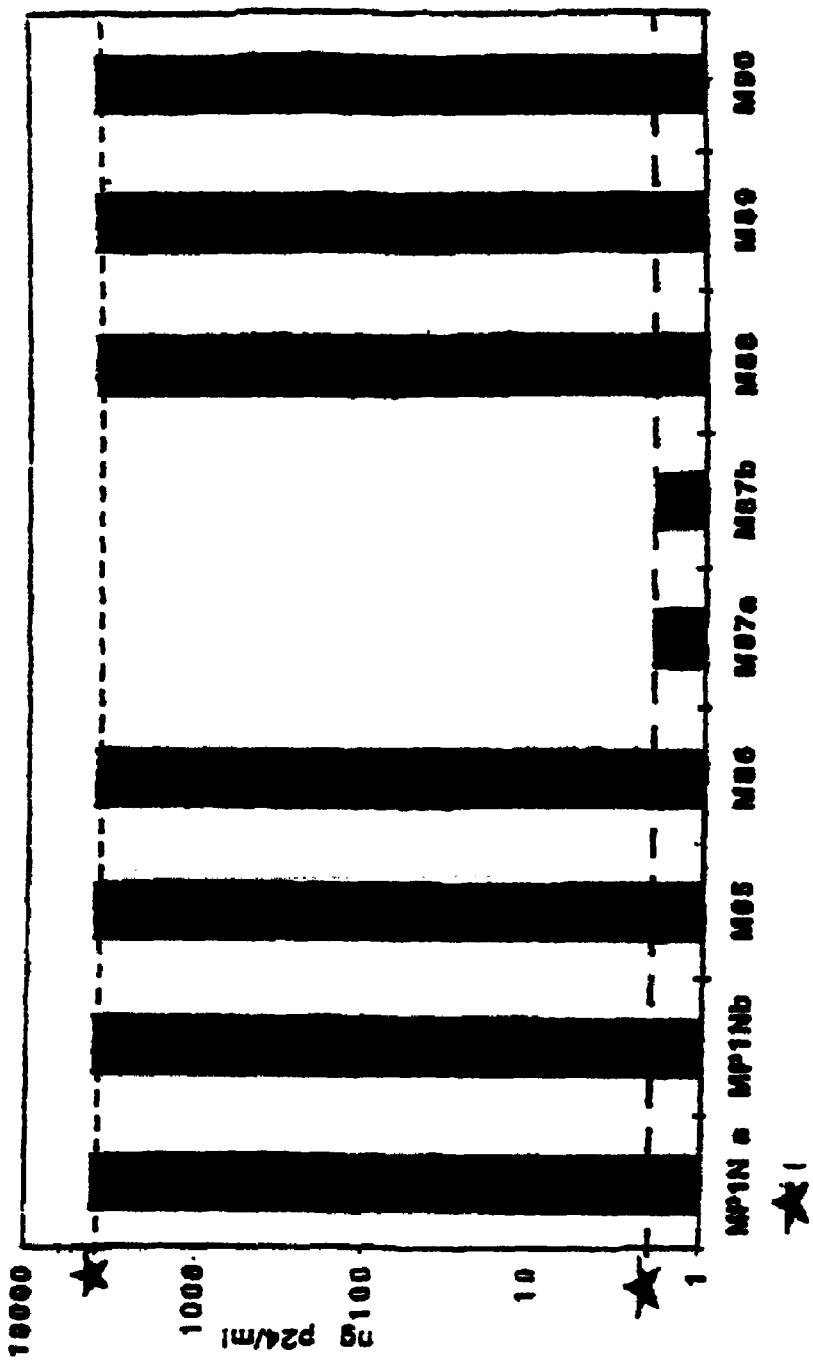
Fig. 2  Detection of HIV Production in lymphocytes with different antiviral vectors on Day 6.

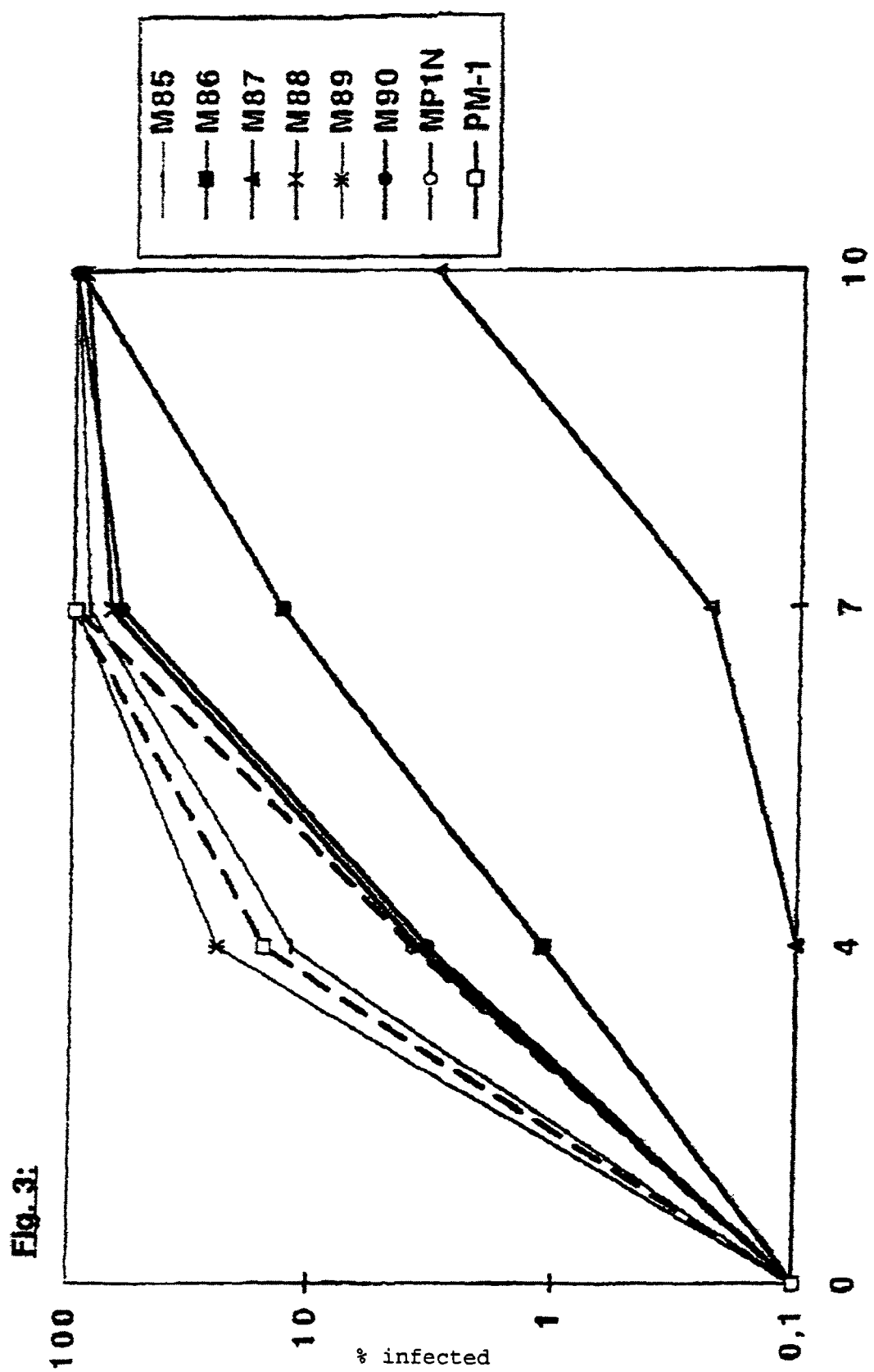

SEQUENCE LISTING

<160> NUMBER OF SEQ ID NOS: 15

<210> SEQ ID NO 1
<211> LENGTH: 4148
<212> TYPE: DNA
<213> ORGANISM: Artificial Sequence
<220> FEATURE:
<223> OTHER INFORMATION: Description of the artificial sequence: M87
      (STHM) - retroviral vector MPIN, which contains 5' of the
      IRES-NEO-cassette an insert encoding membrane-anchored T-20
      peptide
<220> FEATURE:
<221> NAME/KEY: misc_feature
<222> LOCATION: (1438)..(1773)
<223> OTHER INFORMATION: STHM (vector insert containing the region
      encoding membrane-anchored T-20 peptid)
<220> FEATURE:
<221> NAME/KEY: CDS
<222> LOCATION: (1528)..(1773)
<223> OTHER INFORMATION: Region in the M87 (STHM) insert, encoding
      membrane-anchored T-20 fusion protein including signal peptide
<220> FEATURE:
<221> NAME/KEY: sig_peptide
<222> LOCATION: (1438)..(1527)
<220> FEATURE:
<221> NAME/KEY: CDS
<222> LOCATION: (1528)..(1773)
<223> OTHER INFORMATION: T-20 fusion protein with membrane anchor
<220> FEATURE:
<221> NAME/KEY: misc_feature
<222> LOCATION: (1528)..(1635)
<223> OTHER INFORMATION: Region encoding T-20
<220> FEATURE:
<221> NAME/KEY: misc_feature
<222> LOCATION: (1636)..(1683)
<223> OTHER INFORMATION: Region encoding hinge
<220> FEATURE:
<221> NAME/KEY: misc_feature
<222> LOCATION: (1684)..(1773)
<223> OTHER INFORMATION: Region encoding membrane anchor
<220> FEATURE:
<221> NAME/KEY: misc_feature
<222> LOCATION: (1793)..(2421)
<223> OTHER INFORMATION: Polio-IRES
<220> FEATURE:
<221> NAME/KEY: misc_feature
<222> LOCATION: (2380)..(3267)
<223> OTHER INFORMATION: neoR cDNA
<220> FEATURE:
<221> NAME/KEY: misc_feature
<222> LOCATION: (31)..(36)
<223> OTHER INFORMATION: NheI cleavage site
<220> FEATURE:
<221> NAME/KEY: misc_feature
<222> LOCATION: (370)..(377)
<223> OTHER INFORMATION: AscI cleavage site
<220> FEATURE:
<221> NAME/KEY: misc_feature
<222> LOCATION: (400)..(405)
<223> OTHER INFORMATION: XmaI cleavage site
<220> FEATURE:
<221> NAME/KEY: misc_feature
<222> LOCATION: (696)..(701)
<223> OTHER INFORMATION: SacII cleavage site
<220> FEATURE:
<221> NAME/KEY: misc_feature
<222> LOCATION: (1421)..(1426)
<223> OTHER INFORMATION: SacII cleavage site
<220> FEATURE:
<221> NAME/KEY: misc_feature
<222> LOCATION: (1429)..(1436)
<223> OTHER INFORMATION: NotI cleavage site
<220> FEATURE:
<221> NAME/KEY: misc_feature
<222> LOCATION: (1775)..(1780)
<223> OTHER INFORMATION: SalI cleavage site

```
<220> FEATURE:
<221> NAME/KEY: misc_feature
<222> LOCATION: (1787)..(1792)
<223> OTHER INFORMATION: SphI cleavage site
<220> FEATURE:
<221> NAME/KEY: misc_feature
<222> LOCATION: (1793)..(1798)
<223> OTHER INFORMATION: HindIII cleavage site
<220> FEATURE:
<221> NAME/KEY: misc_feature
<222> LOCATION: (2422)..(2429)
<223> OTHER INFORMATION: NotI cleavage site
<220> FEATURE:
<221> NAME/KEY: misc_feature
<222> LOCATION: (3002)..(3007)
<223> OTHER INFORMATION: SphI cleavage site
<220> FEATURE:
<221> NAME/KEY: misc_feature
<222> LOCATION: (3447)..(3452)
<223> OTHER INFORMATION: HindIII cleavage site
<220> FEATURE:
<221> NAME/KEY: misc_feature
<222> LOCATION: (3586)..(3591)
<223> OTHER INFORMATION: NheI cleavage site
<220> FEATURE:
<221> NAME/KEY: misc_feature
<222> LOCATION: (4000)..(4007)
<223> OTHER INFORMATION: AscI cleavage site
<220> FEATURE:
<221> NAME/KEY: misc_feature
<222> LOCATION: (4030)..(4035)
<223> OTHER INFORMATION: XmaI cleavage site

<400> SEQUENCE: 1
aatgaaagac cccacctgta ggtttggcaa gctagcttaa gtaacgccat tttgcaaggc      60
atggaaaata cataactgag aatagagaag ttcagatcaa ggttaggaac agagagacag     120
cagaatatgg gccaaacagg atatctgtgg taagcagttc ctgccccgct cagggccaag     180
aacagatggt ccccagatgc ggtcccgccc tcagcagttt ctagagaacc atcagatgtt     240
tccagggtgc cccaaggacc tgaaaatgac cctgtgcctt atttgaacta accaatcagt     300
tcgcttctcg cttctgttcg cgcgcttctg ctccccgagc tcaataaaag agcccacaac     360
ccctcactcg gcgcgccagt cctccgattg actgagtcgc ccgggtaccc gtgttctcaa     420
taaaccctct tgcagttgca tccgactcgt ggtctcgctg atccttggga gggtctcctc     480
agattgattg actgcccacc tcggggggtct ttcatttgga ggttccaccg agatttggag     540 accctgccc agggaccacc gacccccccg ccgggaggta agctggccag cggtcgtttc     600
gtgtctgtct ctgtctttgt gcgtgtttgt gccggcatct aatgtttgcg cctgcgtctg     660
tactagttgg ctaactagat ctgtatctgg cggtcccgcg gaagaactga cgagttcgta     720
ttcccggccg cagcccctgg gagacgtccc agcggcctcg ggggcccgtt ttgtggccca     780
ttctgtatca gttaacctac ccgagtcgga cttttttggag ctccgccact gtccgagggg     840
tacgtggctt tgttggggga cgagagacag agacacttcc cgccccgtc tgaattttg      900 ctttcggttt tacgccgaaa ccgcgccgcg cgtcttgtct gctgcagcat cgttctgtgt     960
tgtctctgtc tgactgtgtt tctgtatttg tctgaaaatt agggccagac tgttaccact    1020
cccttaagtt tgaccttagg tcactggaaa gatgtcgagc ggatcgctca caaccagtcg    1080
gtagatgtca agaagagacg ttgggttacc ttctgctctg cagaatggcc aacctttaac    1140
gtcggatggc cgcgagacgg cacctttaac cgagacctca tcacccaggt taagatcaag    1200
gtcttttcac ctggcccgca tggacaccca gaccaggtcc cctacatcgt gacctgggaa    1260
gccttggctt ttgacccccc tccctgggtc aagccctttg tacacctaa gcctccgcct    1320
```

-continued

```
cctcttcctc catccgcccc gtctctcccc cttgaacctc ctcgttcgac cccgcctcga   1380
tcctcccttt atccagccct cactccttct ctaggcgcca ccgcggtggc ggccgcc      1437 atg ggg gca ggt gcc acc ggc cgc gcc atg gac ggg ccg cgc ctg ctg    1485
Met Gly Ala Gly Ala Thr Gly Arg Ala Met Asp Gly Pro Arg Leu Leu
 1               5                  10                  15 ctg ttg ctg ctt ctg ggg gtg tcc ctt gga ggt gcc aga tct tac act    1533
Leu Leu Leu Leu Leu Gly Val Ser Leu Gly Gly Ala Arg Ser Tyr Thr
                 20                  25                  30 agc tta ata cac tcc tta att gaa gaa tcg caa aac cag caa gaa aag    1581
Ser Leu Ile His Ser Leu Ile Glu Glu Ser Gln Asn Gln Gln Glu Lys
             35                  40                  45 aat gaa caa gaa tta ttg gaa tta gat aaa tgg gca agt ttg tgg aat    1629
Asn Glu Gln Glu Leu Leu Glu Leu Asp Lys Trp Ala Ser Leu Trp Asn
 50                  55                  60 tgg ttt aga tct gtt cca aga gac tgt gga tgc aaa ccc tgt ata tgt    1677
Trp Phe Arg Ser Val Pro Arg Asp Cys Gly Cys Lys Pro Cys Ile Cys
 65                  70                  75                  80 acc ctc atc cct gtc tat tgc tcc atc ctg gct gct gtg gtt gtg ggc    1725
Thr Leu Ile Pro Val Tyr Cys Ser Ile Leu Ala Ala Val Val Val Gly
                 85                  90                  95 ctt gtg gcc tac ata gcc ttc aag agg tgg aac agg ggg atc ctc tag    1773
Leu Val Ala Tyr Ile Ala Phe Lys Arg Trp Asn Arg Gly Ile Leu
                100                 105                 110 agtcgacctg caggcatgca agcttaaaac agctctgggg ttgtacccac cccagaggcc   1833
cacgtggcgg ctagtactcc ggtattgcgg taccttgta cgcctgtttt atactccctt   1893
cccgtaactt agacgcacaa aaccaagttc aatagaaggg ggtacaaacc agtaccacca  1953
cgaacaagca cttctgtttc cccggtgatg tcgtatacac tgcttgcgtg gttgaaagcg  2013
acggatccgt tatccgctta tgtacttcga aagcccagt accacctcgg aatctcaatg   2073
cgttgcgctc agcactcaac cccatagtgt acttaggctg atgagtctcc acatccctca  2133
ccggtgacgg tggtccaggt tgcgttggcg gcctacctat ggctaacgcc atgggacgct  2193
agttgtgaac aaggtgtgaa gagcctattg agctacataa gaatcctccg gccctgaat   2253 gcggctaatc ccaaccctcg gagcaggtgg tcacaaacca gtgattggcc tgtcgtaacg  2313
cgaagtccgt ggcggaaccg actactttgg gtgtccgtgt ttccttttat tttattgtgg  2373
ctgcttatgg tgacaatcac agattgttat cataaagcga attggattgc ggccgctcta  2433
gaactagtgg atctaattcc tgcagccaat atgggatcgg ccattgaaca agatggattg  2493
cacgcaggtt ctccggccgc ttgggtggag aggctattcg ctatgactg gcacaacag    2553 acaatcggct gctctgatgc cgccgtgttc cggctgtcag cgcaggggcg cccggttctt  2613
tttgtcaaga ccgacctgtc cggtgccctg aatgaactgc aggacgaggc agcgcggcta  2673
tcgtggctgg ccacgacggg cgttccttgc gcagctgtgc tcgacgttgt cactgaagcg  2733
ggaagggact ggctgctatt gggcgaagtg ccggggcagg atctcctgtc atctcacctt  2793
gctcctgccg agaaagtatc catcatggct gatgcaatgc ggcggctgca tacgcttgat  2853
ccggctacct gcccattcga ccaccaagcg aaacatcgca tcgagcgagc acgtactcgg  2913
atggaagccg gtcttgtcga tcaggatgat ctggacgaag agcatcaggg gctcgcgcca  2973
gccgaactgt tcgccaggct caaggcgcgc atgcccgacg cgaggatct cgtcgtgacc   3033 catggcgatg cctgcttgcc gaatatcatg gtggaaaatg gccgcttttc tggattcatc  3093
gactgtggcc ggctgggtgt ggcggaccgc tatcaggaca tagcgttggc tacccgtgat  3153
attgctgaag agcttggcgg cgaatgggct gaccgcttcc tcgtgcttta cggtatcgcc  3213
```

-continued

```
gctcccgatt cgcagcgcat cgccttctat cgccttcttg acgagttctt ctgagcggga      3273
ctctggggtt cgaaatgacc gaccaagcga cgcccaacct gccatcacga gatttcgatt      3333
ccaccgccgc cttctatgaa aggttgggct tcggaatcgt tttccgggac gccggctgga      3393
tgatcctcca gcgcggggat ctcatgctgg agttcttcgc ccaccccgga tccaagctta      3453
tcgataggcc taggcctatc gataggccta ggctatcga taggcctaac acgagccata      3513
gatagaataa agattttat ttagtctcca gaaaaggggg ggaatgaaag accccacctg       3573
taggtttggc aagctagctt aagtaagcca ttttgcaagg catggaaaaa tacataactg      3633
agaatagaga agttcagatc aaggttagga acagagagac aggagaatat gggccaaaca      3693
ggatatctgt ggtaagcagt tcctgccccg gctcagggcc aagaacagtt ggaacagcag      3753
aatatgggcc aaacaggata tctgtggtaa gcagttcctg ccccggctca gggccaagaa      3813
cagatggtcc ccagatgcgg tcccgccctc agcagtttct agagaaccat cagatgtttc      3873
cagggtgccc caaggacctg aaatgaccct gtgccttatt tgaactaacc aatcagttcg      3933
cttctcgctt ctgttcgcgc gcttctgctc cccgagctca ataaaagagc ccacaacccc      3993
tcactcggcg cgccagtcct ccgatagact gcgtcgcccg gggtacccgt attcccaata      4053
aagcctcttg ctgtttgcat ccgaatcgtg gactcgctga tccttgggag ggtctcctca      4113
gattgattga ctgcccacct cggggggtctt tcatt                                4148
```

<210> SEQ ID NO 2
<211> LENGTH: 111
<212> TYPE: PRT
<213> ORGANISM: Artificial Sequence
<220> FEATURE:
<223> OTHER INFORMATION: synthetic

<400> SEQUENCE: 2

```
Met Gly Ala Gly Ala Thr Gly Arg Ala Met Asp Gly Pro Arg Leu Leu
 1               5                  10                  15

Leu Leu Leu Leu Leu Gly Val Ser Leu Gly Gly Ala Arg Ser Tyr Thr
             20                  25                  30

Ser Leu Ile His Ser Leu Ile Glu Glu Ser Gln Asn Gln Gln Glu Lys
         35                  40                  45

Asn Glu Gln Glu Leu Leu Glu Leu Asp Lys Trp Ala Ser Leu Trp Asn
     50                  55                  60

Trp Phe Arg Ser Val Pro Arg Asp Cys Gly Cys Lys Pro Cys Ile Cys
 65                  70                  75                  80

Thr Leu Ile Pro Val Tyr Cys Ser Ile Leu Ala Ala Val Val Gly
                 85                  90                  95

Leu Val Ala Tyr Ile Ala Phe Lys Arg Trp Asn Arg Gly Ile Leu
            100                 105                 110
```

<210> SEQ ID NO 3
<211> LENGTH: 2562
<212> TYPE: DNA
<213> ORGANISM: Human immunodeficiency virus type 1
<220> FEATURE:
<221> NAME/KEY: CDS
<222> LOCATION: (1)..(2562)
<223> OTHER INFORMATION: Region encoding envelope glycoprotein of HIV-1

<400> SEQUENCE: 3

```
atg aga gtg aag gag aag tat cag cac ttg tgg aga tgg ggg tgg aaa       48
Met Arg Val Lys Glu Lys Tyr Gln His Leu Trp Arg Trp Gly Trp Lys
 1               5                  10                  15
```

| | | | | | | | | | | | | | | | |
|---|---|---|---|---|---|---|---|---|---|---|---|---|---|---|---|
| tgg | ggc | acc | atg | ctc | ctt | ggg | ata | ttg | atg | atc | tgt | agt | gct | aca | gaa | 96 |
| Trp | Gly | Thr | Met | Leu | Leu | Gly | Ile | Leu | Met | Ile | Cys | Ser | Ala | Thr | Glu | |
| | | | 20 | | | | | 25 | | | | | 30 | | | |
| aaa | ttg | tgg | gtc | aca | gtc | tat | tat | ggg | gta | cct | gtg | tgg | aag | gaa | gca | 144 |
| Lys | Leu | Trp | Val | Thr | Val | Tyr | Tyr | Gly | Val | Pro | Val | Trp | Lys | Glu | Ala | |
| | | 35 | | | | | 40 | | | | | 45 | | | | |
| acc | acc | act | cta | ttt | tgt | gca | tca | gat | gct | aaa | gca | tat | gat | aca | gag | 192 |
| Thr | Thr | Thr | Leu | Phe | Cys | Ala | Ser | Asp | Ala | Lys | Ala | Tyr | Asp | Thr | Glu | |
| | 50 | | | | | 55 | | | | | 60 | | | | | |
| gta | cat | aat | gtt | tgg | gcc | aca | cat | gcc | tgt | gta | ccc | aca | gac | ccc | aac | 240 |
| Val | His | Asn | Val | Trp | Ala | Thr | His | Ala | Cys | Val | Pro | Thr | Asp | Pro | Asn | |
| 65 | | | | | 70 | | | | | 75 | | | | | 80 | |
| cca | caa | gaa | gta | gta | ttg | gta | aat | gtg | aca | gaa | aat | ttt | aac | atg | tgg | 288 |
| Pro | Gln | Glu | Val | Val | Leu | Val | Asn | Val | Thr | Glu | Asn | Phe | Asn | Met | Trp | |
| | | | | 85 | | | | | 90 | | | | | 95 | | |
| aaa | aat | gac | atg | gta | gaa | cag | atg | cat | gag | gat | ata | atc | agt | tta | tgg | 336 |
| Lys | Asn | Asp | Met | Val | Glu | Gln | Met | His | Glu | Asp | Ile | Ile | Ser | Leu | Trp | |
| | | | 100 | | | | | 105 | | | | | 110 | | | |
| gat | caa | agc | cta | aag | cca | tgt | gta | aaa | tta | acc | cca | ctc | tgt | gtt | agt | 384 |
| Asp | Gln | Ser | Leu | Lys | Pro | Cys | Val | Lys | Leu | Thr | Pro | Leu | Cys | Val | Ser | |
| | | 115 | | | | | 120 | | | | | 125 | | | | |
| tta | aag | tgc | act | gat | ttg | aag | aat | gat | act | aat | acc | aat | agt | agt | agc | 432 |
| Leu | Lys | Cys | Thr | Asp | Leu | Lys | Asn | Asp | Thr | Asn | Thr | Asn | Ser | Ser | Ser | |
| | 130 | | | | | 135 | | | | | 140 | | | | | |
| ggg | aga | atg | ata | atg | gag | aaa | gga | gag | ata | aaa | aac | tgc | tct | ttc | aat | 480 |
| Gly | Arg | Met | Ile | Met | Glu | Lys | Gly | Glu | Ile | Lys | Asn | Cys | Ser | Phe | Asn | |
| 145 | | | | | 150 | | | | | 155 | | | | | 160 | |
| atc | agc | aca | agc | ata | aga | gat | aag | gtg | cag | aaa | gaa | tat | gca | ttc | ttt | 528 |
| Ile | Ser | Thr | Ser | Ile | Arg | Asp | Lys | Val | Gln | Lys | Glu | Tyr | Ala | Phe | Phe | |
| | | | | 165 | | | | | 170 | | | | | 175 | | |
| tat | aaa | ctt | gat | ata | gta | cca | ata | gat | aat | acc | agc | tat | agg | ttg | ata | 576 |
| Tyr | Lys | Leu | Asp | Ile | Val | Pro | Ile | Asp | Asn | Thr | Ser | Tyr | Arg | Leu | Ile | |
| | | | 180 | | | | | 185 | | | | | 190 | | | |
| agt | tgt | aac | acc | tca | gtc | att | aca | cag | gcc | tgt | cca | aag | gta | tcc | ttt | 624 |
| Ser | Cys | Asn | Thr | Ser | Val | Ile | Thr | Gln | Ala | Cys | Pro | Lys | Val | Ser | Phe | |
| | | 195 | | | | | 200 | | | | | 205 | | | | |
| gag | cca | att | ccc | ata | cat | tat | tgt | gcc | ccg | gct | ggt | ttt | gcg | att | cta | 672 |
| Glu | Pro | Ile | Pro | Ile | His | Tyr | Cys | Ala | Pro | Ala | Gly | Phe | Ala | Ile | Leu | |
| | 210 | | | | | 215 | | | | | 220 | | | | | |
| aaa | tgt | aat | aat | aag | acg | ttc | aat | gga | aca | gga | cca | tgt | aca | aat | gtc | 720 |
| Lys | Cys | Asn | Asn | Lys | Thr | Phe | Asn | Gly | Thr | Gly | Pro | Cys | Thr | Asn | Val | |
| 225 | | | | | 230 | | | | | 235 | | | | | 240 | |
| agc | aca | gta | caa | tgt | aca | cat | gga | atc | agg | cca | gta | gta | tca | act | caa | 768 |
| Ser | Thr | Val | Gln | Cys | Thr | His | Gly | Ile | Arg | Pro | Val | Val | Ser | Thr | Gln | |
| | | | | 245 | | | | | 250 | | | | | 255 | | |
| ctg | ctg | tta | aat | ggc | agt | cta | gca | gaa | gaa | gat | gta | gta | att | aga | tct | 816 |
| Leu | Leu | Leu | Asn | Gly | Ser | Leu | Ala | Glu | Glu | Asp | Val | Val | Ile | Arg | Ser | |
| | | | 260 | | | | | 265 | | | | | 270 | | | |
| gcc | aat | ttc | aca | gac | aat | gct | aaa | acc | ata | ata | gta | cag | ctg | aac | aca | 864 |
| Ala | Asn | Phe | Thr | Asp | Asn | Ala | Lys | Thr | Ile | Ile | Val | Gln | Leu | Asn | Thr | |
| | | 275 | | | | | 280 | | | | | 285 | | | | |
| tct | gta | gaa | att | aat | tgt | aca | aga | ccc | aac | aac | aat | aca | aga | aaa | agt | 912 |
| Ser | Val | Glu | Ile | Asn | Cys | Thr | Arg | Pro | Asn | Asn | Asn | Thr | Arg | Lys | Ser | |
| | 290 | | | | | 295 | | | | | 300 | | | | | |
| atc | cgt | atc | cag | agg | gga | cca | ggg | aga | gca | ttt | gtt | aca | ata | gga | aaa | 960 |
| Ile | Arg | Ile | Gln | Arg | Gly | Pro | Gly | Arg | Ala | Phe | Val | Thr | Ile | Gly | Lys | |
| 305 | | | | | 310 | | | | | 315 | | | | | 320 | |
| ata | gga | aat | atg | aga | caa | gca | cat | tgt | aac | att | agt | aga | gca | aaa | tgg | 1008 |
| Ile | Gly | Asn | Met | Arg | Gln | Ala | His | Cys | Asn | Ile | Ser | Arg | Ala | Lys | Trp | |

-continued

```
                325                 330                 335
aat gcc act tta aaa cag ata gct agc aaa tta aga gaa caa ttt gga        1056
Asn Ala Thr Leu Lys Gln Ile Ala Ser Lys Leu Arg Glu Gln Phe Gly
            340                 345                 350 aat aat aaa aca ata atc ttt aag caa tcc tca gga ggg gac cca gaa        1104
Asn Asn Lys Thr Ile Ile Phe Lys Gln Ser Ser Gly Gly Asp Pro Glu
        355                 360                 365 att gta acg cac agt ttt aat tgt gga ggg gaa ttt ttc tac tgt aat        1152
Ile Val Thr His Ser Phe Asn Cys Gly Gly Glu Phe Phe Tyr Cys Asn
    370                 375                 380 tca aca caa ctg ttt aat agt act tgg ttt aat agt act tgg agt act        1200
Ser Thr Gln Leu Phe Asn Ser Thr Trp Phe Asn Ser Thr Trp Ser Thr
385                 390                 395                 400 gaa ggg tca aat aac act gaa gga agt gac aca atc aca ctc cca tgc        1248
Glu Gly Ser Asn Asn Thr Glu Gly Ser Asp Thr Ile Thr Leu Pro Cys
                405                 410                 415 aga ata aaa caa ttt ata aac atg tgg cag gaa gta gga aaa gca atg        1296
Arg Ile Lys Gln Phe Ile Asn Met Trp Gln Glu Val Gly Lys Ala Met
            420                 425                 430 tat gcc cct ccc atc agt gga caa att aga tgt tca tca aat att act        1344
Tyr Ala Pro Pro Ile Ser Gly Gln Ile Arg Cys Ser Ser Asn Ile Thr
        435                 440                 445 ggg ctg cta tta aca aga gat ggt ggt aat aac aac aat ggg tcc gag        1392
Gly Leu Leu Leu Thr Arg Asp Gly Gly Asn Asn Asn Asn Gly Ser Glu
    450                 455                 460 atc ttc aga cct gga gga gga gat atg agg gac aat tgg aga agt gaa        1440
Ile Phe Arg Pro Gly Gly Gly Asp Met Arg Asp Asn Trp Arg Ser Glu
465                 470                 475                 480 tta tat aaa tat aaa gta gta aaa att gaa cca tta gga gta gca ccc        1488
Leu Tyr Lys Tyr Lys Val Val Lys Ile Glu Pro Leu Gly Val Ala Pro
                485                 490                 495 acc aag gca aag aga aga gtg gtg cag aga gaa aaa aga gca gtg gga        1536
Thr Lys Ala Lys Arg Arg Val Val Gln Arg Glu Lys Arg Ala Val Gly
            500                 505                 510 ata gga gct ttg ttc ctt ggg ttc ttg gga gca gca gga agc act atg        1584
Ile Gly Ala Leu Phe Leu Gly Phe Leu Gly Ala Ala Gly Ser Thr Met
        515                 520                 525 ggc tgc acg tca atg acg ctg acg gta cag gcc aga caa tta ttg tct        1632
Gly Cys Thr Ser Met Thr Leu Thr Val Gln Ala Arg Gln Leu Leu Ser
    530                 535                 540 gat ata gtg cag cag cag aac aat ttg ctg agg gct att gag gcg caa        1680
Asp Ile Val Gln Gln Gln Asn Asn Leu Leu Arg Ala Ile Glu Ala Gln
545                 550                 555                 560 cag cat ctg ttg caa ctc aca gtc tgg ggc atc aaa cag ctc cag gca        1728
Gln His Leu Leu Gln Leu Thr Val Trp Gly Ile Lys Gln Leu Gln Ala
                565                 570                 575 aga atc ctg gct gtg gaa aga tac cta aag gat caa cag ctc ctg ggg        1776
Arg Ile Leu Ala Val Glu Arg Tyr Leu Lys Asp Gln Gln Leu Leu Gly
            580                 585                 590 att tgg ggt tgc tct gga aaa ctc att tgc acc act gct gtg cct tgg        1824
Ile Trp Gly Cys Ser Gly Lys Leu Ile Cys Thr Thr Ala Val Pro Trp
        595                 600                 605 aat gct agt tgg agt aat aaa tct ctg gaa cag att tgg aat aac atg        1872
Asn Ala Ser Trp Ser Asn Lys Ser Leu Glu Gln Ile Trp Asn Asn Met
    610                 615                 620 acc tgg atg gag tgg gac aga gaa att aac aat tac aca agc tta ata        1920
Thr Trp Met Glu Trp Asp Arg Glu Ile Asn Asn Tyr Thr Ser Leu Ile
625                 630                 635                 640 cac tcc tta att gaa gaa tcg caa aac cag caa gaa aag aat gaa caa        1968
```

-continued

```
                His Ser Leu Ile Glu Glu Ser Gln Asn Gln Gln Glu Lys Asn Glu Gln
                                645                 650                 655 gaa tta ttg gaa tta gat aaa tgg gca agt ttg tgg aat tgg ttt aac                    2016
Glu Leu Leu Glu Leu Asp Lys Trp Ala Ser Leu Trp Asn Trp Phe Asn
            660                 665                 670 ata aca aat tgg ctg tgg tat ata aaa tta ttc ata atg ata gta gga                    2064
Ile Thr Asn Trp Leu Trp Tyr Ile Lys Leu Phe Ile Met Ile Val Gly
        675                 680                 685 ggc ttg gta ggt tta aga ata gtt ttt gct gta ctt tct ata gtg aat                    2112
Gly Leu Val Gly Leu Arg Ile Val Phe Ala Val Leu Ser Ile Val Asn
    690                 695                 700 aga gtt agg cag gga tat tca cca tta tcg ttt cag acc cac ctc cca                    2160
Arg Val Arg Gln Gly Tyr Ser Pro Leu Ser Phe Gln Thr His Leu Pro
705                 710                 715                 720 atc ccg agg gga ccc gac agg ccc gaa gga ata gaa gaa gaa ggt gga                    2208
Ile Pro Arg Gly Pro Asp Arg Pro Glu Gly Ile Glu Glu Glu Gly Gly
                725                 730                 735 gag aga gac aga gac aga tcc att cga tta gtg aac gga tcc tta gca                    2256
Glu Arg Asp Arg Asp Arg Ser Ile Arg Leu Val Asn Gly Ser Leu Ala
            740                 745                 750 ctt atc tgg gac gat ctg cgg agc ctg tgc ctc ttc agc tac cac cgc                    2304
Leu Ile Trp Asp Asp Leu Arg Ser Leu Cys Leu Phe Ser Tyr His Arg
        755                 760                 765 ttg aga gac tta ctc ttg att gta acg agg att gtg gaa ctt ctg gga                    2352
Leu Arg Asp Leu Leu Leu Ile Val Thr Arg Ile Val Glu Leu Leu Gly
    770                 775                 780 cgc agg ggg tgg gaa gcc ctc aaa tat tgg tgg aat ctc cta cag tat                    2400
Arg Arg Gly Trp Glu Ala Leu Lys Tyr Trp Trp Asn Leu Leu Gln Tyr
785                 790                 795                 800 tgg agt cag gaa cta aag aat agt gct gtt aac ttg ctc aat gcc aca                    2448
Trp Ser Gln Glu Leu Lys Asn Ser Ala Val Asn Leu Leu Asn Ala Thr
                805                 810                 815 gcc ata gca gta gct gag ggg aca gat agg gtt ata gaa gta tta caa                    2496
Ala Ile Ala Val Ala Glu Gly Thr Asp Arg Val Ile Glu Val Leu Gln
            820                 825                 830 gca gct tat aga gct att cgc cac ata cct aga aga ata aga cag ggc                    2544
Ala Ala Tyr Arg Ala Ile Arg His Ile Pro Arg Arg Ile Arg Gln Gly
        835                 840                 845 ttg gaa agg att ttg cta                                                            2562
Leu Glu Arg Ile Leu Leu
    850

<210> SEQ ID NO 4
<211> LENGTH: 854
<212> TYPE: PRT
<213> ORGANISM: Human immunodeficiency virus type 1

<400> SEQUENCE: 4

Met Arg Val Lys Glu Lys Tyr Gln His Leu Trp Arg Trp Gly Trp Lys
1               5                   10                  15

Trp Gly Thr Met Leu Leu Gly Ile Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
```

-continued

```
                85                  90                  95
Lys Asn Asp Met Val Glu Gln Met His Glu Asp Ile Ile Ser Leu Trp
            100                 105                 110
Asp Gln Ser Leu Lys Pro Cys Val Lys Leu Thr Pro Leu Cys Val Ser
            115                 120                 125
Leu Lys Cys Thr Asp Leu Lys Asn Asp Thr Asn Thr Asn Ser Ser Ser
            130                 135                 140
Gly Arg Met Ile Met Glu Lys Gly Glu Ile Lys Asn Cys Ser Phe Asn
145                 150                 155                 160
Ile Ser Thr Ser Ile Arg Asp Lys Val Gln Lys Glu Tyr Ala Phe Phe
                165                 170                 175
Tyr Lys Leu Asp Ile Val Pro Ile Asp Asn Thr Ser Tyr Arg Leu Ile
            180                 185                 190
Ser Cys Asn Thr Ser Val Ile Thr Gln Ala Cys Pro Lys Val Ser Phe
            195                 200                 205
Glu Pro Ile Pro Ile His Tyr Cys Ala Pro Ala Gly Phe Ala Ile Leu
            210                 215                 220
Lys Cys Asn Asn Lys Thr Phe Asn Gly Thr Gly Pro Cys Thr Asn Val
225                 230                 235                 240
Ser Thr Val Gln Cys Thr His Gly Ile Arg Pro Val Val Ser Thr Gln
                245                 250                 255
Leu Leu Leu Asn Gly Ser Leu Ala Glu Glu Asp Val Val Ile Arg Ser
            260                 265                 270
Ala Asn Phe Thr Asp Asn Ala Lys Thr Ile Ile Val Gln Leu Asn Thr
            275                 280                 285
Ser Val Glu Ile Asn Cys Thr Arg Pro Asn Asn Asn Thr Arg Lys Ser
            290                 295                 300
Ile Arg Ile Gln Arg Gly Pro Gly Arg Ala Phe Val Thr Ile Gly Lys
305                 310                 315                 320
Ile Gly Asn Met Arg Gln Ala His Cys Asn Ile Ser Arg Ala Lys Trp
                325                 330                 335
Asn Ala Thr Leu Lys Gln Ile Ala Ser Lys Leu Arg Glu Gln Phe Gly
            340                 345                 350
Asn Asn Lys Thr Ile Ile Phe Lys Gln Ser Ser Gly Gly Asp Pro Glu
            355                 360                 365
Ile Val Thr His Ser Phe Asn Cys Gly Gly Glu Phe Phe Tyr Cys Asn
            370                 375                 380
Ser Thr Gln Leu Phe Asn Ser Thr Trp Phe Asn Ser Thr Trp Ser Thr
385                 390                 395                 400
Glu Gly Ser Asn Asn Thr Glu Gly Ser Asp Thr Ile Thr Leu Pro Cys
                405                 410                 415
Arg Ile Lys Gln Phe Ile Asn Met Trp Gln Glu Val Gly Lys Ala Met
            420                 425                 430
Tyr Ala Pro Pro Ile Ser Gly Gln Ile Arg Cys Ser Ser Asn Ile Thr
            435                 440                 445
Gly Leu Leu Leu Thr Arg Asp Gly Gly Asn Asn Asn Gly Ser Glu
            450                 455                 460
Ile Phe Arg Pro Gly Gly Gly Asp Met Arg Asp Asn Trp Arg Ser Glu
465                 470                 475                 480
Leu Tyr Lys Tyr Lys Val Val Lys Ile Glu Pro Leu Gly Val Ala Pro
                485                 490                 495
Thr Lys Ala Lys Arg Arg Val Val Gln Arg Glu Lys Arg Ala Val Gly
            500                 505                 510
```

```
Ile Gly Ala Leu Phe Leu Gly Phe Leu Gly Ala Ala Gly Ser Thr Met
            515                 520                 525
Gly Cys Thr Ser Met Thr Leu Thr Val Gln Ala Arg Gln Leu Leu Ser
        530                 535                 540
Asp Ile Val Gln Gln Gln Asn Asn Leu Leu Arg Ala Ile Glu Ala Gln
545                 550                 555                 560
Gln His Leu Leu Gln Leu Thr Val Trp Gly Ile Lys Gln Leu Gln Ala
                565                 570                 575
Arg Ile Leu Ala Val Glu Arg Tyr Leu Lys Asp Gln Gln Leu Leu Gly
            580                 585                 590
Ile Trp Gly Cys Ser Gly Lys Leu Ile Cys Thr Thr Ala Val Pro Trp
        595                 600                 605
Asn Ala Ser Trp Ser Asn Lys Ser Leu Glu Gln Ile Trp Asn Asn Met
            610                 615                 620
Thr Trp Met Glu Trp Asp Arg Glu Ile Asn Asn Tyr Thr Ser Leu Ile
625                 630                 635                 640
His Ser Leu Ile Glu Glu Ser Gln Asn Gln Gln Glu Lys Asn Glu Gln
                645                 650                 655
Glu Leu Leu Glu Leu Asp Lys Trp Ala Ser Leu Trp Asn Trp Phe Asn
            660                 665                 670
Ile Thr Asn Trp Leu Trp Tyr Ile Lys Leu Phe Ile Met Ile Val Gly
        675                 680                 685
Gly Leu Val Gly Leu Arg Ile Val Phe Ala Val Leu Ser Ile Val Asn
            690                 695                 700
Arg Val Arg Gln Gly Tyr Ser Pro Leu Ser Phe Gln Thr His Leu Pro
705                 710                 715                 720
Ile Pro Arg Gly Pro Asp Arg Pro Glu Gly Ile Glu Glu Glu Gly Gly
                725                 730                 735
Glu Arg Asp Arg Asp Arg Ser Ile Arg Leu Val Asn Gly Ser Leu Ala
            740                 745                 750
Leu Ile Trp Asp Asp Leu Arg Ser Leu Cys Leu Phe Ser Tyr His Arg
        755                 760                 765
Leu Arg Asp Leu Leu Leu Ile Val Thr Arg Ile Val Glu Leu Leu Gly
        770                 775                 780
Arg Arg Gly Trp Glu Ala Leu Lys Tyr Trp Trp Asn Leu Leu Gln Tyr
785                 790                 795                 800
Trp Ser Gln Glu Leu Lys Asn Ser Ala Val Asn Leu Leu Asn Ala Thr
                805                 810                 815
Ala Ile Ala Val Ala Glu Gly Thr Asp Arg Val Ile Glu Val Leu Gln
            820                 825                 830
Ala Ala Tyr Arg Ala Ile Arg His Ile Pro Arg Arg Ile Arg Gln Gly
        835                 840                 845
Leu Glu Arg Ile Leu Leu
    850

<210> SEQ ID NO 5
<211> LENGTH: 30
<212> TYPE: DNA
<213> ORGANISM: Artificial sequence
<220> FEATURE:
<223> OTHER INFORMATION: Description of artificial sequence: primer
      SPNot+

<400> SEQUENCE: 5
gcggccgcca tggggcagg tgccaccggc                                    30
```

<210> SEQ ID NO 6
<211> LENGTH: 30
<212> TYPE: DNA
<213> ORGANISM: Artificial sequence
<220> FEATURE:
<223> OTHER INFORMATION: Description of artificial sequence: primer SPBgl2-

<400> SEQUENCE: 6
agatctggca cctccaaggg acaccccag                                30

<210> SEQ ID NO 7
<211> LENGTH: 30
<212> TYPE: DNA
<213> ORGANISM: Artificial sequence
<220> FEATURE:
<223> OTHER INFORMATION: Description of artificial sequence: primer T20Bgl+

<400> SEQUENCE: 7
agatcttaca ctagcttaat acactcctta                               30

<210> SEQ ID NO 8
<211> LENGTH: 39
<212> TYPE: DNA
<213> ORGANISM: Artificial sequence
<220> FEATURE:
<223> OTHER INFORMATION: Description of artificial sequence: primer T20Bgl-RGD+

<400> SEQUENCE: 8
agatctagag gcgactacac tagcttaata cactcctta                     39

<210> SEQ ID NO 9
<211> LENGTH: 33
<212> TYPE: DNA
<213> ORGANISM: Artificial sequence
<220> FEATURE:
<223> OTHER INFORMATION: Description of artificial sequence: primer T20Hind-

<400> SEQUENCE: 9
aagcttatta aaccaattc cacaaacttg ccc                            33

<210> SEQ ID NO 10
<211> LENGTH: 54
<212> TYPE: DNA
<213> ORGANISM: Artificial sequence
<220> FEATURE:
<223> OTHER INFORMATION: Description of artificial sequence: primer hingeTMBgl+

<400> SEQUENCE: 10
agatctgttc caagagactg tggatgcaaa ccctgtatat gtaccctcat ccct    54

<210> SEQ ID NO 11
<211> LENGTH: 21
<212> TYPE: DNA
<213> ORGANISM: Artificial sequence
<220> FEATURE:
<223> OTHER INFORMATION: Description of artificial sequence: primer U3-

<400> SEQUENCE: 11
cgcgcgaaca gaagcgagaa g                                        21

```
<210> SEQ ID NO 12
<211> LENGTH: 29
<212> TYPE: DNA
<213> ORGANISM: Artificial sequence
<220> FEATURE:
<223> OTHER INFORMATION: Description of artificial sequence: primer
      T20Bgl-

<400> SEQUENCE: 12
agatctaaac caattccaca aacttgccc                              29

<210> SEQ ID NO 13
<211> LENGTH: 52
<212> TYPE: DNA
<213> ORGANISM: Artificial sequence
<220> FEATURE:
<223> OTHER INFORMATION: Description of artificial sequence: primer
      RGD-T20Not+

<400> SEQUENCE: 13
aaagcggccg ccatgagggg cgattacact agcttaatac actccttaat tg    52

<210> SEQ ID NO 14
<211> LENGTH: 43
<212> TYPE: DNA
<213> ORGANISM: Artificial sequence
<220> FEATURE:
<223> OTHER INFORMATION: Description of artificial sequence: primer
      T20Not+

<400> SEQUENCE: 14
aaagcggccg ccatgtacac tagcttaata cactccttaa ttg              43

<210> SEQ ID NO 15
<211> LENGTH: 60
<212> TYPE: DNA
<213> ORGANISM: Artificial sequence
<220> FEATURE:
<223> OTHER INFORMATION: Description of artificial sequence: primer
      T20mtsHind-

<400> SEQUENCE: 15
aagcttacta gggtgcggca agaagaacag ggagaagaac ggctgcaaac caattccaca   60
```

MEMBRANE-ANCHORED GP41 PEPTIDES THAT INHIBIT SUBSEQUENT HIV VIRAL ENTRY

This application is based on international application PCT/EP00/11733, having an international filing date of Nov. 24, 2000; and claiming priority to German application 199 57 838.9, filed Nov. 25, 1999.

The invention relates to the gene therapy of HIV infection by the expression of membrane-anchored gp41 peptides. With this treatment vectors are made available for the first time which code for a fusion protein that contains a peptide derived from gp41 of HIV and a carboxy terminal transmembrane anchor connected by a flexible linker.

A very wide variety of therapeutic approaches have been proposed for the treatment of HIV infections. However, the active substances available have proved to be poorly tolerated by many patients. To improve AIDS therapy, new points of attack and active substances with different toxicity profiles are constantly being sought. In this context, various gene therapeutical approaches have already been proposed, to inhibit the different steps in HIV replication (cf. Sorg T. & Methali, M. *Transfus. Sci.* 18, 277-289 (1977)).

Wild et al. (Wild, C. T. Shugars, D. C. Greenwell, T. K. McDanal, C. B. & Matthews, T. J. *Proc. Natl. Acad. Sci U.S.A.* 91, 9770-9774 (1994)) have proposed a therapeutic approach based on the observation that peptides which are derived from the trans-membrane protein gp41 (cf. SEQ ID NO: 4 corresponding to the numeric code <400> in accordance with WIPO Standard ST. 25:4) of HIV, such as, for example, the peptide T-20, formerly known as DP178, can effectively inhibit HIV fusion and entry into the cell. T-20 is a peptide which overlaps with the C-terminal heptad repeat, one of two domains (cf. positions 539-589 and 622-662 of SEQ ID NO: 4) in the ectodomain of the gp41, and can effectively inhibit the HIV infection in vitro (Weissenhborn, W., Dessen., A., Harrison, S. C. Skehel, J. J & Wiley, D. C. *Nature* 387, 426-430 (1997); Chan, D. C. Fass, D., Berger, J. M. & Kim, P. S. *Cell* 89. 263-273 (1997); Furuta, R. A., Wild, C. T., Weng Y & Weiss, C. D. *Nat. Struct. Biol.* 5, 276-279 (1998)).

Within the context of a clinical study (Kilby, J. M., Hopkins S., Venetta, T. M. et al. *Nat. Med.* 4, 1302-1307 (1998)), in the case of short-term administration T-20 proved to be safe and effectively inhibit HIV replication. As, however, very large quantities of the peptide are needed, to achieve an antiviral effect and as the peptides are not bio-available if administered orally, possess a very short half-life, and production on a large scale is still extremely expensive, the object of the invention is to make possible intracellular immunisation with peptides which are derived from gp41, via a gene therapeutical approach.

The inventors therefore first cloned the sequences coding for T-20 5' of the IRES-NEO-Cassette (IRES: Internal ribosomal entry site; NEO: Neomycin-resistance gene) of the retroviral vector MPIN (cf. FIG. 1, Hildinger et al., *Hum. Gene Ther.* 9 (1998) 33-42). To achieve the secretion of the T-20, on the one hand the peptide was expressed directly behind the signal peptide of the human low affinity nerve growth factor receptor (LNGFR, Fehse et al., *Human Gene Therapy* 8 (1997) 1815) (Constructs M85 and M86), and on the other hand a construct was chosen, which contains the coding sequences for a membrane-translocation signal (mts) derived from Kaposi fibroblast growth factor (amino acid positions 43-58 in mts protein; Rojas, M., Donahue, J. P., Tan, Z., Lin, Y. Z. *Nat. Biotechnol.* 16, 370-375 (1998)) in frame with T20 (cf. constructs M89 and M90 in FIG. 1). Using these constructs, retroviral vectors were produced by transfection of Phoenix packaging cells (Grignani, F., Kinsella, T., Mencarelli, A. et al., *Cancer Res.* 58, 14-19 (1998)), and the supernatants were used to infect the T-helper cell line PM-1 (Bou-Habib, D. C. et al., *J. Virol.* 68 6006-6013 (1994)). As a control, the MPIN vector was used, which exclusively contains the neomycin resistance gene as a foreign gene. After G418 selection, the mass cultures were infected with HIV-1, which was produced from the proviral clones NL4-3 (Adachi, A., Gendelman H. E., Koenig, S., Folks, T., Willey, R., Rabson, A. & Martin, M. A., *J. Virol.* 59 284-291 (1986)) or NL4-3/GFP (Welker, R., Harris, M., Cardel, B. & Krausslich, H. G. *J., Virol.* 72, 8833-8840 (1998)). These two clones differ in that, in the case of NL4-3/GFP, the green fluorescent protein (GFP) is expressed instead of the nef protein, so that the HIV-1 replication can be analyzed on the basis of the p24 antigen production and/or by flow cytometry. Contrary to all expectations, the expression of T-20 peptide using the above-mentioned retroviral vector constructs however surprisingly led to no antiviral activity of any kind.

Into these constructs, a sequence coding for the integrin-binding RGD peptide in frame with the region coding for T-20 was cloned. The production of these constructs was based on the consideration that the RGD motif could hold the secreting peptides on the cell membrane. However, even with the RGD-containing secreted T-20 peptide (cf. FIG. 1, M86) a reproducible HIV-replication was still observed.

Within the context of the present invention, it has now surprisingly been ascertained that the production of p24 and the spread of NL4-3/GFP can be greatly reduced, if a fusion protein is expressed, which, in addition to an amino-terminal gp41 peptide, contains a trans-membrane anchor tagged thereto carboxyterminally via a flexible linker. In this context, the term "gp41 peptide" means a fragment of the gp41 protein of the HIV or a fragment, variant or mutant thereof.

It has, for example, been ascertained, that the p24 production can be reduced by more than 2 powers of ten, if PM-1 is transduced with a retroviral vector, which expresses a fusion protein in which T-20 is connected C-terminally via a flexible peptide linker with a trans-membrane peptide (membrane spanning domain, MSD) (cf. FIG. 1, M87), wherein the fusion protein has the sequence indicated in SEQ ID NO: 2.

The subject of the present invention is therefore a nucleic acid sequence of the general formula 5'-SP-FI-Hinge-MSD-3', in which "5'" denotes the 5'end of the nucleic acid sequence, "3'" denotes the 3'end of the nucleic acid sequence, "SP" codes for a signal peptide, which mediates the transfer of an expressed peptide into the endoplasmatic reticulum.

"FI" codes for a fragment of the gp41 protein of HIV (preferably HIV-1), which contains a section from a heptad repeat region, "MSD" codes for a trans-membrane-anchor of a type-1 membrane protein and "Hinge" codes for a protein sequence, which, as a flexible linker, connects the peptides encoded by "FI" and "MSD".

The sequence coding for the signal peptide is derived from human, non-immunogenic proteins, preferably selected from the group consisting of sequences which code for signal peptides of cellular membrane proteins, such as, for example of the (human) low affinity nerve growth factor receptor (LNGFR), of the interleukin-2-receptor (IL-2R) and of the granulocyte macrophage colony stimulating factor receptor (GM-CSFR).

As trans-membrane anchors of a type-1 membrane protein (i.e. of a membrane protein, whose N-terminus is located outside and whose C-terminus is located inside the cell), proteins are used, whose cytoplasmatic domain should be deleted, to avoid any undesired signal transduction through the protein. In preliminary tests, it can be clarified that no signal transduction effects emanate from the expressed regions, and they do not oligomerise with other, similar membrane proteins and in this way exert an indirect effect on the cell functions. Peptides from the group consisting of the trans-membrane region of the LNGFR or the CD34 are preferably considered. The nucleic acid sequence therefore preferably contains as MSD, a nucleic acid sequence coding for these trans-membrane anchors and/or a nucleic acid sequence coding for fragments with a deleted cytoplasmatic domain.

According to the invention, it is possible to use, as flexible linkers, all flexible peptides which enable a flexible connection between the gp41 peptide and the trans-membrane anchor, such as, for example, the hinge of immunoglobin G (IgG), the linker of the human P-Glycoprotein (C. A. Hrycyna et al., *Biochemistry* 37 13660-13673 (1998)), the C-terminal linker of the Human Replication Protein A (hsRPA; cf. D. M. Jacobs et al., *J. Biomol. NMR* 14, 321-331 (1999)) and the linker of the parathyroid hormone-related protein (M. Weidler et al. *FEBS Lett.* 444, 239-244 (1999)). The linker preferably has a length of up to 30 amino acids. The nucleic acid sequence of the above formula according to the invention therefore contains a nucleic acid sequence section coding for such a linker, preferably the hinge of IgG corresponding to nucleotides 1636 to 1683 of SEQ ID NO: 1.

As already mentioned, FI codes for a peptide (designated as gp41 peptide) which corresponds to a sequence section of the HIV-gp4'-protein (cf. SEQ ID NO: 4, including the gp41 protein of the HIV quasi-species (clades)), which is selected from a region which includes the two heptad repeat regions (cf. amino acid positions 539-589 and 622-662 in SEQ ID NO: 3 and 4). In this context "HIV" includes all HIV types, especially HIV-1. In this context it is, for example, to be expected that use of an HIV-2 gp41 peptide will result in cross-reactivity with HIV-1 and vice-versa.

The gp41 peptides encoded by FI preferably have a minimum length of 28 amino acids, so that FI includes at least 84 nucleotides. Within the context of the present invention, in particular a nucleic acid sequence coding for the amino acid sequence represented in SEQ ID NO: 2 from Position 31 to 66 (corresponds to peptide T-20) is used as FI, preferably the sequence represented in SEQ ID NO: 1 from nucleotide 1528 to nucleotide 1635. According to a particular embodiment, the peptide encoded by FI has a maximum length of 40 amino acids, corresponding to a maximum length of 120 bases for the coding region FI.

According to a particular embodiment of the invention, the nucleic acid sequence of the general formula "SP-FI-Hinge-MSD" has the sequence represented in SEQ ID NO: 1 from nucleotide 1438 to nucleotide 1773, which codes for the fusion protein represented in SEQ ID NO: 2. A further subject of the invention is the fusion protein encoded in each case by the abovementioned vectors/nucleic acid sequences, of the general formula $$NH_2\text{-sp-fi-hinge-msd-COOH},$$

in which

"$NH_2$" denotes the amino-terminal end of the protein

"COOH" denotes the carboxy-terminal end of the protein

"sp" is a signal peptide, which enables the transfer of an expressed peptide into the endoplasmatic reticulum, "fi" is a fragment of the gp41 protein of HIV, which contains a section from a heptad repeat region, "msd" is a trans-membrane anchor of a type I membrane protein and "hinge" is a protein sequence which connects the "fi" and "msd" peptides as a flexible linker.

With regard to the definitions of "sp", "fi", "hinge" and "msd", reference should be made to the above definitions of the sequence elements "SP", "FI, "Hinge" and "MSD", where the structural and functional characteristics of the fusion protein and/or the individual partial regions of the protein have already been mentioned.

According to a preferred embodiment, the fusion protein has the amino acid sequence represented in SEQ ID NO: 2. The fusion protein ("fi-hinge-msd") obtained therefrom after the cleaving off of the signal peptide accordingly has the sequence shown in SEQ ID NO: 2 from Position 31 to Position 111.

Also included according to the invention are homologues and/or variants and fragments of the abovementioned fusion protein, which essentially have the same pharmacological and biological effectiveness and/or immunogenicity and the nucleic acid sequences coding for these homologues and fragments. In this context, the terms "homologues" and "variants" mean sequences which differ from the natural sequences or sequence sections known hitherto, by the exchange, deletion or insertion of individual amino acids. In this context in particular homologues, variants and fragments of the protein represented in SEQ ID NO: 2 and the nucleic acid sequences encoding the same are included.

The invention further relates to a vector which contains one above-mentioned nucleic acid sequence. The vector is preferably a retroviral vector.

According to a preferred embodiment of the invention, the vector has the structure represented in FIG. 1. The vector-insert of the general formula "SP-FI-Hinge-MSD", encoding the fusion protein according to the invention, preferably has the nucleic acid sequence represented in SEQ ID NO: 1. A sample of the last-mentioned vector was deposited with the German Collection of Microorganisms and Cell Cultures (DSMZ), Mascheroder Weg 1b, 38124 Brunswick, Germany, on Nov. 11, 1999, under number DSM 13139 under the Budapest Treaty.

The abovementioned vector can be used for the in vitro transfection of T-lymphocytes and haematopoietic stem cells, whereby these transfected cells can be administered to HIV-infected patients for therapeutic treatment. The vectors according to the invention are especially suitable for use (i.e. for direct (in vivo) application) in gene therapeutical treatment of patients infected with HIV, in which case the vectors are preferably vectors with targeted tropism, i.e. with specificity towards HIV target cells (CD4+ cells). The invention further relates to a gene therapeutical medicament, which contains an abovementioned vector.

The invention is further explained below, with reference to examples.

BRIEF DESCRIPTION OF DRAWINGS

The above and other objects, features, and advantages of the present invention will be better understood from the following detailed description taken in conjunction with the accompanying drawings, all of which are given by way of illustration only, and are not limitative of the present invention, in which:

FIG. 1: (A) and (B) set forth the IRES NEO-Cassette of the retroviral vector MPIN.

FIG. 2: Detection of HIV production in lymphocytes with MP1Na, MP1Nb, M85, M86, M87a, M87b, M88, M89, and M90 vectors on day 6.

FIG. 3: The percentage of EGFP-positive and HIV-infected cells at 0, 4, 7, and 10 days as monitored by flow cytometry for M85, M86, M87, M88, M89, M90, MP1N, and PM-1 cultures.

FIG. 4: Detection of HIV replication in HXB, YU2, JR-FL, and VSV-G pseudotypes.

EXAMPLES

Cells and Viruses

HeLa-, 293- and Phoenix-Ampho cells were cultivated in Dulbecco's Medium (Gibco, Paisley, Great Britain), which was supplemented with 10% foetal calf serum (FCS; Sigma, Deisenhofen, Germany). PM-1 was cultivated in RPMI with 10% FCS. The viral clones NL4-3/GFP, NL4-3env-GFP and pNL4-3 have already been described above. (NL4-3: Welker R., Harris, M., Cardel, B. & Krausslich, H. G. *J. Virol.* 72, 8833-8840 (1998); NL4-2env-GFP: He, J. Chen, Y., Farzan, M., et al. *Nature* 385, 645-649 (1997)). To pseudotype the env-deficient clone NL4-3env-GFP, the plasmids pSNJG, pSVIIIenvJRFL, pSVIIIenvYU2 and pSVIIIenvHXB2 (Welker, R., Harris, M., Cardel, B. & Krausslich, H. G. *J. Virol.* 72, 8833-8840 (1998); He, J. Chen, Y., Farzan, M., et al. *Nature* 385, 645-649 (1997); von Laer, D., Thomson, S., Vogt, B., et al., *J. Virol* 72, 1424-1430 (1998)) were used. These plasmids contain the VSV G-cDNA or the cDNA of the HIV envelopes JR-FL, YU2 and HXB2.

Infectious replication-competent viruses were produced by transfection of NL4-3 or NL4-3/GFP-DNA in HeLa cells. Pseudotyped replication-incompetent HIV were produced by co-transfection of pNL4-3env-GFP and one of the envelope-expression plasmids in 293-cells. The retroviral vectors were packaged in Phoenix packaging cells as described above (Grignani, F., Kinsella, T., Mencarelli, A., et al., *Cancer Res.* 58, 14-19 (1998)).

Cloning of Retroviral Vectors

M85 and M86: The sequence coding for the signal peptide of the human low affinity nerve growth factor receptor (LNGFR) was amplified by polymerase chain reaction (PCR) starting from the vector dLN using the primers SPNot+ (Sequence ID NO: 5) and SPBg12 (SEQ ID NO: 6), whereby a NotI cleavage site was inserted at the 5' end and a BglII cleavage site was inserted at the 3' end (dLN: Fehse et al., Human Gene Therapy 8 (1997) 1815). The sequence coding for the fusion-inhibiting peptide was amplified from NL4-3 using the primer T20Bgl+ (M85; SEQ ID NO: 7) or T20Bgl-RGD+ (M86; SEQ ID NO: 8) and T20Hind– (SEQ NO ID: 9), whereby a BglII cleavage site was inserted at the 5' end and a HindIII cleavage site was inserted at the 3' end. The fragments were ligated into the vector pBluescriptKS digested with NotI and HindIII.

M87 and M88: The trans-membrane domain of dLNGFR was amplified from dLN using a 5' primer, which also contains that for the hinge-region of the murine IgG heavy chain and a BglII cleavage site (hingeTMBgl+; SEQ ID NO: 10), and a 3' primer of the retroviral vector dLN (U3–; sequence ID NO: 11). This PCR product was inserted, together with the signal peptide PCR product (SPNot+/SPBgl–) into the vector pBluescriptKS (after digestion with NotI and HindIII), and the sequence for T20 (starting from NL4-3) was inserted subsequently as PCR product, which contains flanking BglII cleavage sites (by using the PCR primer T20Bgl+ corresponding to SEQ ID NO: 7 (see above) and T20Bgl– corresponding to SEQ ID NO: 12).

M89 and M90: The sequence coding for T20 with a membrane translocation signal (mts) was amplified from NL4-3 using the primer RGD-T20Not+ (M89; SEQ ID NO: 13) or T20NotI (M90; SEQ ID NO: 14) and T20mtsHind– (SEQ ID NO: 15). In the 5' primer, a NotI cleavage site is present, and in the 3' primer there is a HindIII cleavage site. The membrane translocation signal (mts) was introduced with the 3' primer. The product was inserted into the vector pBluescriptKS digested with NotI and HindIII.

The genes encoding the different T20-fusion proteins were then transferred as NotI×HindIII fragments together with the polio-IRES from SF1 MIN into the vector MP1N (Hildinger et al., Hum. Gene Ther. 9 (1998) 33-42).

Infection with HIV

PM-1-cells ($5 \times 10^4$ in 0.5 ml) were infected with 3000 to 6000 TCID50 (tissue culture infectious dose 50%) replication-competent HIV. For analysis of the p24 production the medium was changed on day 5, the cells were incubated overnight, and the cell-free residues were examined using a p24 ELISA as described above (Konvalinka, J., Litterst., M. A., Welker, R., et al. *J. Virol.* 69, 7180-7186 (1995)). The results are represented in FIG. 2.

Infection with NL4-3/GFP was further monitored at the moments indicated by means of flow cytometry analysis with a FACScalibur (Beckton Dickinson, Heidelberg, Germany). For this purpose, PM-1 (with and without the vectors MP1N and M85 to M87) were infected with a moi of 0.01 (moi: multiplicity of infection; describes the number of virus particles with which a cell is infected) with NL-4/GFP and analysed by flow cytometry on days 4, 7 and 10. The percentage of EGFP-positive and thus HIV-infected cells is shown in FIG. 3 in course for the various cultures. The detection threshold is approx. 0.1% positive cells.

Examination of the Mechanism of Action

To determine at which stage the HIV replication is inhibited, "single round" infections were carried out with the clone NL4-3env-GFP. The clone NL4-3env-GFP, due to a mutation in the env-gene is replication-defective and expresses GFP instead of nef. To produce infectious virions, the vector was pseudotyped with the envelopes of three different HIV clones (HXB, YU2 and JR-FL) and with the G protein of the vesicular stomatitis virus (VSV G). HXB is classified as T-tropic, with use of the co-receptor CXCR4, whilst YU2 and JR-FL are M-tropic and use CCR-5. The env-genes of the last two clones mentioned were cloned directly from primary HIV isolates (He, J., Chen, Y., Farzan, M. et al. *Nature* 385, 645-649 (1997)). These HIV pseudotypes are capable of "single round" infections, but do not spread throughout the whole culture. In PM1/M87 cells (i.e. in cells which are transfected with the vector according to the invention, encoding the membrane-anchored T-20 fusion protein) the infection was more strongly inhibited via the three different HIV envelopes, by a factor of 15 to 30, than in the case of the VSV-G pseudotypes, in which no significant inhibition was observed (cf. FIG. 4). Just like the free T-20 peptide (cf. Wild C. T. et al. *Proc. Natl. Acad. Sci. USA* 91, 9770-9774), the genetically expressed membrane-anchored T-20 fusion protein also inhibits entry mediated via the envelopes of the different HIV variants. These results clearly show that the virus is inhibited at the stage of virus entry mediated via HIV-env, in which it is very probably a matter of membrane fusion. All HIV-replication steps following the virus entry were not influenced.

These investigations show that membrane-anchored gp41 peptide effectively inhibits HIV replication, whilst secreted pure gp41 peptide is not effective.

The invention claimed is:

1. A nucleic acid molecule encoding a fusion protein comprising four linked polypeptides comprising:
   (a) a first sequence encoding a membrane translocation signal peptide;
   (b) a second sequence encoding a section of a gp41 protein comprising at least 28 amino acids of a heptad repeat region;
   (c) a third sequence encoding a transmembrane anchor of a type 1 membrane protein; and
   (d) a hinge sequence that connects said second sequence and said third sequence, wherein said hinge sequence encodes a flexible linker from a protein selected from the group consisting of immunoglobulin G (IgG), human P-glycoprotein, human replication protein A and parathyroid hormone-related protein.

2. The nucleic acid molecule of claim 1, wherein said signal peptide is a signal peptide from a protein selected from the group consisting of the low affinity nerve growth factor receptor (LNGFR), the interleukin-2 receptor (IL-2R), and the granulocyte macrophage colony-stimulating factor receptor (GM-CSFR).

3. The nucleic acid molecule of claim 2, wherein said transmembrane anchor is selected from a transmembrane anchor of a type 1 membrane protein is selected from the group consisting of LNGFR and CD34.

4. The nucleic acid molecule of claim 1, wherein said heptad repeat region is selected from the group consisting of the amino acid sequence from any HIV type corresponding to positions 539-589 or 622-662 of SEQ ID NO: 4.

5. The nucleic acid molecule of claim 4, wherein said HIV type is HIV-1.

6. A vector comprising the nucleic acid molecule of claim 1.

7. The vector of claim 6, wherein said vector is a retroviral vector.

8. The nucleic acid molecule of claim 1, wherein said second sequence encodes a maximum length of 40 amino acids and said hinge sequence encodes a maximum length of 30 amino acids.

9. The nucleic acid molecule of claim 1, wherein
(a) said signal peptide from a protein is selected from the group consisting of the low affinity nerve growth factor receptor (LNGFR), the interleukin-2 receptor (IL-2R), and the granulocyte macrophage colony-stimulating factor receptor (GM-CSFR);
(b) said heptad repeat region is selected from the group consisting of the amino acid sequence from any HIV type corresponding to positions 539-589 or 622-662 of SEQ ID NO: 4; and
(c) said transmembrane anchor is selected from a transmembrane anchor of a type 1 membrane protein selected from the group consisting of LNGFR and CD34.

10. The nucleic acid molecule of claim 1, wherein said heptad repeat region is selected from the amino acid sequence from any HIV type corresponding to positions 622-662 of SEQ ID NO: 4.

11. The nucleic acid molecule of claim 1, wherein
(a) said signal peptide is low affinity nerve growth factor receptor (LNGFR);
(b) said heptad repeat region is selected from the group consisting of the amino acid sequence from any HIV type corresponding to positions 622-662 of SEQ ID NO: 4;
(c) said transmembrane anchor is CD34; and
(d) wherein said hinge sequence encodes a immunoglobulin G (IgG) flexible linker.

12. A vector comprising SEQ ID NO: 1.

13. The vector of claim 12, deposited with the German Collection of Microorganisms and Cell Cultures under the number DSM 13139.

14. A nucleic acid molecule encoding SEQ ID NO: 2.

15. A fusion protein with three linked amino acid sequences comprising:
(a) a section of a gp41 protein of HIV comprising at least 28 amino acids from a heptad repeat region;
(b) a transmembrane anchor of a type 1 membrane protein; and
(c) a flexible linker that connects said section of a gp41 protein of HIV and said trans-membrane anchor of a type 1 membrane protein, wherein said flexible linker is from a protein selected from the group consisting of immunoglobulin G (IgG), human P-glycoprotein, human replication protein A and parathyroid hormone-related protein; wherein said fusion protein, when expressed on the surface of a mammalian cell, inhibits subsequent HIV viral entry.

16. The fusion protein of claim 15, wherein said heptad repeat region is selected from the group consisting of the amino acid sequences from any HIV type corresponding to positions 539-589 or 622-662 of SEQ ID NO: 4.

17. The fusion protein of claim 15, wherein said heptad repeat region corresponds to positions 622-662 of SEQ ID NO: 4.

18. The fusion protein of claim 15, wherein said heptad repeat region corresponds to positions 31-66 of SEQ ID NO: 2.

19. A nucleic acid molecule encoding a fusion protein comprising four linked polypeptides comprising:
(a) a first sequence encoding a membrane translocation signal peptide;
(b) a second sequence encoding a section of a gp41 protein comprising at least 28 amino acids from any HIV type corresponding to positions 31 to 66 of SEQ ID NO: 2;
(c) a third sequence encoding a transmembrane anchor of a type 1 membrane protein; and
(d) a hinge sequence that connects said second sequence and said third sequence, wherein said hinge sequence encodes a flexible linker from a protein selected from the group consisting of immunoglobulin G (IgG), human P-glycoprotein, human replication protein A and parathyroid hormone-related protein; and wherein the expressed fusion protein inhibits subsequent HIV viral entry.

20. The nucleic acid molecule of claim 19, wherein
(a) said signal peptide is low affinity nerve growth factor receptor (LNGFR);
(b) said transmembrane anchor is CD34; and
(c) wherein said hinge sequence encodes a immunoglobulin G (IgG) flexible linker.

* * * * *